United States Patent [19]

Kuboto

[11] Patent Number: 4,706,656
[45] Date of Patent: Nov. 17, 1987

[54] ENDOSCOPE DEVICE WITH TOOL CHANNEL
[75] Inventor: Tetsumaru Kuboto, Tokyo, Japan
[73] Assignee: Olympus Optical Co., Ltd., Tokyo, Japan
[21] Appl. No.: 859,591
[22] Filed: May 5, 1986
[30] Foreign Application Priority Data May 15, 1985 [JP] Japan .................... 60-103442

[51] Int. Cl.⁴ ............................................. A61B 1/06
[52] U.S. Cl. ................................................. 128/6
[58] Field of Search ........................... 128/3, 4, 5, 6, 7

[56] References Cited
U.S. PATENT DOCUMENTS 1,459,313  6/1923  Reisler et al. ............... 128/7
2,797,683  7/1957  Aiken .......................... 128/6
3,261,350  7/1966  Wallace ....................... 128/6
4,146,019  3/1979  Bass et al. ................... 128/6
4,630,598  12/1986 Bonnet ......................... 128/7

FOREIGN PATENT DOCUMENTS 8119209.6  7/1981  Fed. Rep. of Germany .
4786       12/1958 Japan .

Primary Examiner—William H. Grieb
Attorney, Agent, or Firm—Armstrong, Nikaido, Marmelstein & Kubovcik

[57] ABSTRACT

An endoscope device wherein an observing optical system, illuminating optical system and channel are incorporated into respectively independent pipes which are then arranged as exposed out to form an endoscope inserting part and the above mentioned channel is formed to be of a noncircular cross-section so that, when a treating tool is inserted through the channel, a larger hollow gap may be made between the inner wall of the channel and the treating tool.

3 Claims, 7 Drawing Figures

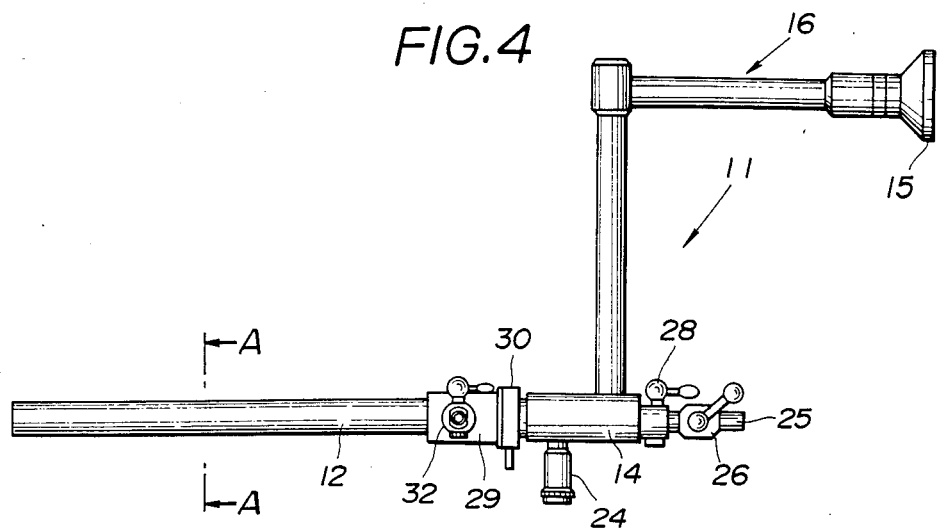
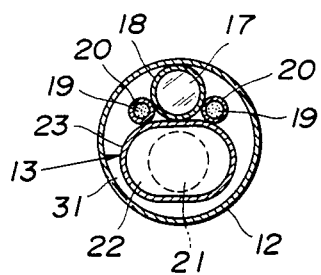
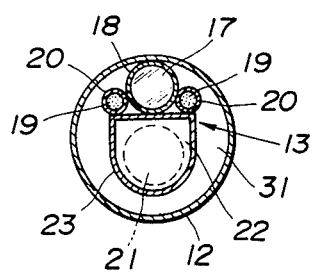
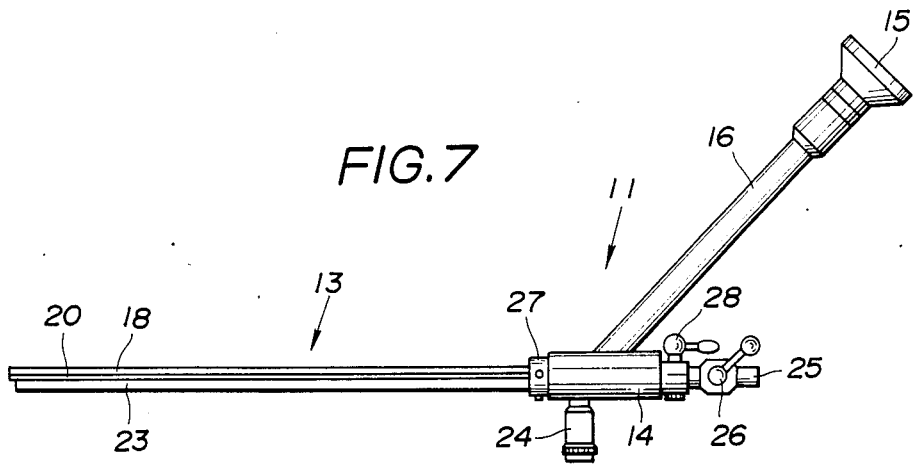

ENDOSCOPE DEVICE WITH TOOL CHANNEL

BACKGROUND OF THE NVENTION

1. Field of the Invention

This invention relates to an endoscope device improved so that, when a treating tool is used, the irrigated amount within the channel may be sufficiently secured without making the diameter of the inserting part larger.

2. Related Art Statement

There is recently extensively used an endoscope wherein the elongated inserting part is to be inserted into a body cavity so that organs within the body cavity may be observed, a tissue within the living body may be taken out to diagnose particularly the affected part by using such treating tool as a forceps inserted through a channel as required and such various treatments may be made.

There are a soft endoscope wherein the inserting part is soft and curvable and a rigid endoscope wherein the inserting part is rigid and substantially linear.

A rigid endoscope of a type having a channel is shown, for example, in the publication of a West German utility model application laid open No. G 8119209.6. This is an endoscope wherein a tube of an oval cross-section is provided within an outer tube of a circular cross-section, an observing optical system and a conduit in which a probe is inserted are arranged within the tube of the oval cross-section and photoconductors are contained and arranged in hollow gaps enclosed with the outer peripheries of the above mentioned observing optical system and the conduit and the inner periphery of the tube of the oval cross-section.

An endoscope of a formation related with it is also shown in FIGS. 1 and 2. That is to say, in this endoscope 1, an optical system pipe 3 within which an observing optical system is provided and a channel 4 circular or semicircular in the cross-section and comparatively large in the diameter are inserted and arranged within an outer pipe 2 forming an inserting part and light guide fibers 5 for an illuminating optical system are inserted and arranged in hollow gaps enclosed with the outer peripheries of the above mentioned optical system pipe 3 and the channel 4 and the inner periphery of the outer pipe 2. This endoscope 1 is to be used as combined with a sheath 6.

Now, in the endoscope of the above mentioned prior art example, the observing optical system, illuminating optical system and channel are integrally incorporated within the outr pipe and therefore the diameter is larger by the thickness of this outer pipe. Therefore, in order to absorb the dimension of the thickness of this outer pipe, it is considered (i) to make the diameter of the sheath larger by that thickness, (ii) to make the diameter of the channel smaller by that thickness, (iii) to make the outside diameter of the observing optical system smaller by that thickness and (iv) to make the thickness of each pipe smaller by that thickness. However, in (i) above, the pain given to the patient will become larger by the outside diameter of the sheath made larger. In (ii) above, by the channel made smaller, the outside diameter of the usable treating tool will become smaller and therefore the effect of the treatment will reduce. In (iii), the capacity of the observing diagnosis will reduce. In (iv), the strength will reduce. There are such problems.

On the other hand, there is a problem that, if the cross-section of the channel 4 is circular as shown in FIG. 1, in a case a treating tool 7 is inserted into the channel 4, the space other than for the treating tool 7 within the channel 4 will become small and the amount of irrigation by using the space will reduce.

By the way, in the publication of a Japanese utility model publication No. 4786/1958 is disclosed an endoscope formed of an observing optical system, lamp, water discharging port and electrode inserting channel which are respectively independent. However, in this endoscope, the channel is of a circular cross-section and is arranged in the center of the endoscope, the clearance within the underside sheath is used as a water feeding path, therefore the diameter of the channel is restricted and no channel of a large diameter is obtained.

OBJECT AND SUMMARY OF THE INVENTION

An object of the present invention is to provide an endoscope wherein the diameter of the endoscope inserting part can be made smaller and the amount of irrigation through the channel when a treating tool is inserted through the channel can be secured.

According to the present invention, an observing optical system, illuminating optical system and channel are incorproated into respectively independent pipes which are then arranged as exposed out to form an endoscope inserting part and the above mentioned channel is formed to be of a noncircular cross-section so that, when a treating tool is inserted through the channel, a larger hollow gap may be made between the inner wall of the channel and the treating tool.

The other features and advantages of the present invention will become apparent enough with the following explanation.

BRIEF DESCRIPTION OF THE DRAWINGS

FIGS. 3 to 5 relate to the first embodiment of the present invention.

FIG. 3 is an elevation of the appearance of the endoscope.

FIG. 4 is an elevation showing the endoscope of FIG. 3 as combined with a sheath.

FIG. 5 is a sectioned view on line A—A in FIG. 4.

FIG. 6 is a sectioned view of an inserting part showing the second embodiment of the present invention.

FIG. 7 is an elevation of an endoscope showing the third embodiment of the present invention.

DETAILED DESCRIPTION OF PREFERRED EMBODIMENTS

Figure 3:
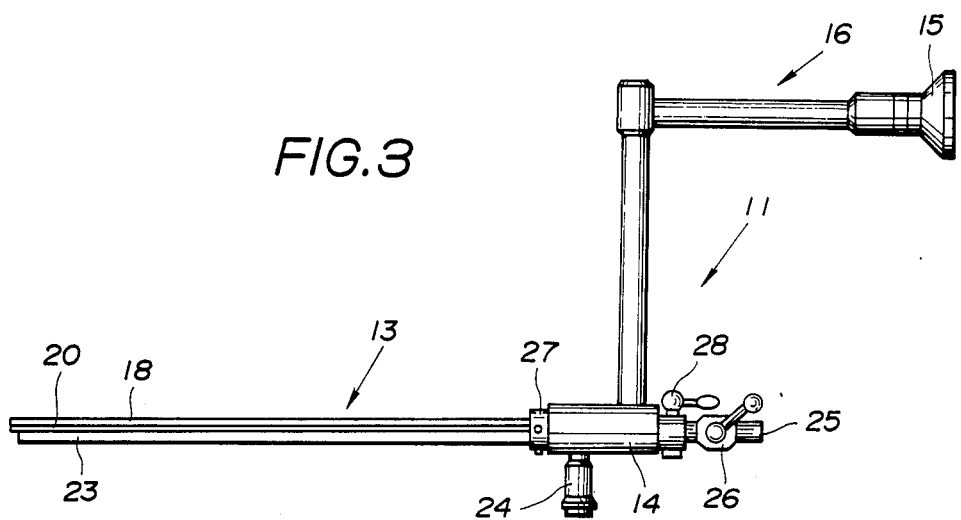

In FIGS. 3 to 5, the reference numeral 11 represents an endoscope to be used as combined with a sheath 12. In this endoscope 11, an elongated inserting part 13 to be inserted into the sheath 12 is extended forward from a body part 14 on the handling side and, on the other hand, an eyepiece part 16 provided with an eyepiece part 15 is projected rearward from the outer periphery of the body part 14. The above mentioned inserting part 13 is formed respectively independently of an optical pipe 18 provided internally with an observing opitcal system 17 transmitting an observed image to the end of the eyepiece 15, light guide pipes 20 filled with light guides 19 for illuminating a position to be observed within a body cavity and a channel pipe 23 within which is formed a channel 22 through which a treating tool 21 is to be inserted. These pipes 18, 20 and 23 are arranged as exposed out without being incorporated within an outer pipe. The above mentioned channel pipe 23 is formed to be of an elliptic cross-section and has the long diameter arranged horizontally. The optical system pipe 18 is arranged in the substantially central axis direction above the outer periphery of the long side of ths channel pipe 23 and the two light guide pipes 20 are arranged symmetrically above the outer periphery of the above mentioned channel pipe 23 on both sides of the optical system pipe 18 so that all the combined cross-sectional area of the channel pipe 23, optical system pipe 18 and light pipes 20 may be compact.

On the other hand, the body part 14 of the above mentioned endoscope 11 is provided on the outer periphery with a projecting light guide mouthpiece 24 for transmitting an illuminating light to the light guides 19 through a light guide cable from an external light source, is provided at the rear end with a treating tool inserting port 25 communicating with the channel 22 and is fitted with a cock 26 for opening and closing the channel 22. This body part 14 is further provided with a sheath connecting part 27 and a cock 28 communicating with the channel 22 to feed an irrigating liquid.

The sheath 12 in which the above mentioned endoscope inserting part 13 is inserted to be combined has in the rear a sheath body 29 on which are arranged an endoscope removably fitting part 30 to fit and connect the sheath connecting part 27 of the endoscope 11 to the sheath body 29 and a cock 32 communicating with the internal cavity 31 of the sheath to discharge the irrigating liquid.

Figure 1:
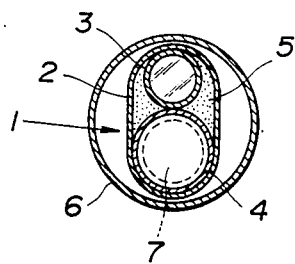
FIGS. 1 and 2 are sectioned views showing prior art examples.
Figure 2:
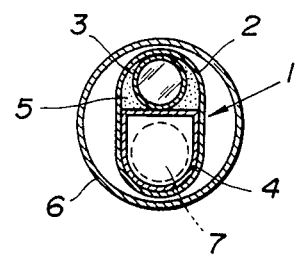

As the inserting part 13 is formed of the optical system pipe 18, light guide pipes 20 and channel pipe 23 respectively independently arranged as mentioed above, such outer pipes as of the prior art examples shown in FIGS. 1 and 2 are not required, the outside diameter of the inserting part 13 can be made smaller by the thickness of various outer pipes and thus the outside diameter of the sheath 12 can be made smaller. Further, as channel pipe 23 is elliptic in the cross-section, when the treating tool 21 is inserted through the channel 22, the hollow space of the channel will be able to be taken to be large and the irrigated amount will be able to be well secured.

Thus, as compared with the prior art examples shown in FIGS. 1 and 2, in case the outside diameter of the sheath 12 is set to be the same as in the prior art examples, the diameter of the channel pipe 23 will be able to be made larger at least by the thickness of the outer pipe made unnecessary, therefore the treating tool 21 of an outside diameter larger than in the prior art examples will be able to be used and the effect of the treatment will be able to be improved. In case the outside diameter of the treating tool 21 to be used is set to be the same as in the prior art example, the outside diameter of the sheath 12 will be able to be made smaller than in the prior art examples and therefore the pain to be given to the patient will be able to be reduced.

Further, in any of the above mentioned cases, even when the treating tool 21 is inserted through the channel 22, the hollow space will be able to be taken to be large, therefore a sufficient irrigated amount will be secured, the visual field of the observing opitcal system 17 will not be obstructed, for example, by bleeding during the treatment and the treatment will be able to be made safely within a short time.

By the way, the irrigation can be made always continuously by feeding the irrigating liquid through the channel 22 from the cock 28 communicating with the channel 22 and at the same time by discharging the irrigating liquid polluted with blood or the like through the cock communicating with the inner cavity 31 of the sheath 12.

FIG. 6 shows the cross-section of the second embodiment of the present invention. In this embodiment, the channel pipe 23 is of a substantially semicircular cross-section and has the same effect as in the above mentioned first embodiment. Though not illustrated, the channel pipe may be of an elliptic, semicircular or modified cross-section.

FIG. 7 shows an elevation of the third embodiment of the present invention. The eyepiece part 16 is arranged parallely with the inserting part 13 in the first embodiment but at an angle with the inserting part 13 in the third embodiment. By the way, this eyepiece part may be varied in the shape and arrangement.

In this invention, it is apparent that working modes different in a wide range can be formed on the basis of this invention without departing from the spirit and scope of the invention. This invention is not restricted by any specific working mode except being limited by the appended claims.

What is claimed is:

1. An endoscope device characterized in that an observing optical systems, illuminating optical system and treatment tool channel are incorporated into respectively independent pipes which are then arranged to form an endoscope inserting part, said treatment tool channel pipe being formed in a noncircular cross-section and having a hollow gap extending axially along the interior of said treatment tool channel pipe between the treating tool and said treatment tool channel pipe when the treatment tool is inserted therethrough.

2. An endoscope device according to claim 1 wherein said treatment tool channel tool pipe is formed in an elliptic cross-section having at least a substantially flat side wall and said observing optical system pipe and said illuminating optical system pipe extend axially along one of the substantially flat outer elongated elliptical wall portions of said treatment tool channel pipe.

3. An endoscope device according to claim 1 wherein said treatment tool channel pipe is formed in a semicircular cross-section having a substantially flat side wall and said observing optical system pipe and said illuminating optical system pipe extend axially along the outer surface of the substantially flat side wall of said treatment tool channel pipe.

* * * * *